United States Patent
Chen

(10) Patent No.: US 10,456,104 B2
(45) Date of Patent: Oct. 29, 2019

(54) UNIVERSAL C-ARM CALIBRATION SEAT

(71) Applicant: Metal Industries Research & Development Centre, Kaohsiung (TW)

(72) Inventor: Ming-Hui Chen, Kaohsiung (TW)

(73) Assignee: Metal Industries Research & Development Centre, Kaohsiung (TW)

(*) Notice: Subject to any disclaimer, the term of this patent is extended or adjusted under 35 U.S.C. 154(b) by 168 days.

(21) Appl. No.: 15/807,923

(22) Filed: Nov. 9, 2017

(65) Prior Publication Data
US 2019/0083055 A1 Mar. 21, 2019

(30) Foreign Application Priority Data
Sep. 20, 2017 (TW) .............................. 106132283 A

(51) Int. Cl.
*A61B 6/00* (2006.01)
*G01T 7/00* (2006.01)

(52) U.S. Cl.
CPC ............ *A61B 6/582* (2013.01); *A61B 6/4441* (2013.01); *G01T 7/005* (2013.01)

(58) Field of Classification Search
CPC ....... A61B 6/585; A61B 6/584; A61B 6/4441; A61B 6/542; A61B 6/548; G01T 7/005; G01T 7/00
USPC .......................................................... 378/207
See application file for complete search history.

(56) References Cited

U.S. PATENT DOCUMENTS 8,007,172 B2 * 8/2011 Marino ................ A61B 6/4405
378/204
2015/0164443 A1 6/2015 Laws et al.

FOREIGN PATENT DOCUMENTS

TW 201228787 A 7/2012

* cited by examiner

*Primary Examiner* — Marcus H Taningco
*Assistant Examiner* — Fani Boosalis
(74) *Attorney, Agent, or Firm* — Alan D. Kamrath; Mayer & Williams PC

(57) ABSTRACT

A universal C-ARM calibration seat includes a base, at least three action units, and a driving and positioning device. The base is annular and has a central axis. The base includes a correction plate mounting area. The at least three action units is mounted on a side of the base opposite to the correction plate mounting area. Each of the at least three action units includes a sliding member. The driving and positioning device is coaxially mounted to and rotatable relative to the base about the central axis. The driving and positioning device includes a rotating unit configured to actuate each sliding member. When the driving and positioning device rotates relative to the base, the rotating unit actuates each sliding member to simultaneously move toward the central axis.

10 Claims, 7 Drawing Sheets

UNIVERSAL C-ARM CALIBRATION SEAT

BACKGROUND

1. Technical Field

The present invention relates to a calibration seat and, more particularly, to a universal C-arm calibration seat that can be coaxially positioned.

2. Description of the Related Art

Surgical navigation systems for 3D C-arm X-ray machines have the feature of high maneuverability and can be used to show the location of a surgical instrument in a human body through a diagnostic imaging technique, which helps a doctor to immediately know the location of the implant or any other tool placed in a patient. Thus, the surgical navigation systems have gradually received attention in spine surgeries and some neurosurgeries. The accuracy of the location of the surgical instrument or the bone nail can be assured by continuously taking pictures using a 3D C-arm.

Furthermore, due to the high average cost of C-arm X-ray systems with 3D technology, a general approach for saving the purchase costs of a 3D C-arm X-ray machine is updating conventional 2D C-arm equipment of different brands into 3D C-arm X-ray systems by connecting a 2D C-arm X-ray system with an external calibration seat of the same brand and using the respective calibration software, which is commonly used in current X-ray image equipment. The coupling between a 2D C-arm and a calibration seat is adjusted by a clamping device to provide a press fit between a reception end of the 2D C-arm and the calibration seat. An example of such a conventional calibration seat is disclosed in Taiwan Patent Publication No. 201228787 entitled "POSITIONING METHOD OF COUPLING A C-ARM AND A GUIDING SYSTEM".

However, positioning of the conventional assembly is achieved through a knob structure of the clamping device, which is difficult for a user to evenly maneuver the displacement and force, such that the calibration seat and the reception end of the 2D C-arm cannot be positioned coaxially, leading to inaccurate surgical navigation alignment and assembling problems in subsequent surgical reproducibility.

Thus, improvement of conventional C-arm calibration seats is necessary.

SUMMARY

To solve the above problems, the present invention provides a universal C-arm calibration seat for use with all types of conventional 2D C-arms available in the market while achieving coaxial positioning and providing assembling convenience.

When the terms "front", "rear", "up", "down", "top", "bottom", "inner", "outer", "side", and similar terms are used herein, it should be understood that these terms have reference only to the structure shown in the drawings as it would appear to a person viewing the drawings and are utilized only to facilitate describing the invention, rather than restricting the invention.

A universal C-ARM calibration seat according to the present invention includes a base, at least three action units, and a driving and positioning device. The base is annular and has a central axis. The base includes a correction plate mounting area. The at least three action units is mounted on a side of the base opposite to the correction plate mounting area. Each of the at least three action units includes a sliding member. The driving and positioning device is coaxially mounted to and rotatable relative to the base about the central axis. The driving and positioning device includes a rotating unit configured to actuate each sliding member. When the driving and positioning device rotates relative to the base, the rotating unit actuates each sliding member to simultaneously move toward the central axis.

In use, the universal C-arm calibration seat according to the present invention is coupled to a reception end of 2D C-arm equipment. The universal C-arm calibration seat uses the interrelationship between the driving and positioning device and the at least three action units, such that when the rotating unit of the driving and positioning device rotates in the counterclockwise direction, the inclined portion of each of the at least three engaging plates presses against a corresponding one of the protrusions. Thus, all sliding members simultaneously move toward the central axis until the abutting portion of each sliding member abuts the outer periphery of the reception end of the 2D C-arm equipment. Then, the positioning member of the driving and positioning device is rotated to a tightened state to achieve a coaxial positioning effect. In addition to easy installation, the universal C-arm calibration seat according to the present invention is suitable for use with all conventional X-ray machines with a 2D C-arm.

In an example, the driving and positioning device includes a positioning unit. When each sliding member is displaced to a predetermined position, the positioning unit restrains rotation of the rotating unit relative to the base. Thus, each sliding member is prevented from disengaging from the outer periphery of the reception end.

In an example, the rotating unit includes a first arcuate plate and at least three engaging plates. The first arcuate plate extends through each of the at least three action units. Each of the at least three engaging plates is disposed in association with one of the at least three action units and is fixed to the first arcuate plate. Each of the at least three engaging plates includes an inclined portion. Each sliding member includes an upper face having a protrusion. The inclined portion of each of at least three engaging plates abuts the protrusion of one of the sliding members to push each sliding member toward the central axis.

In an example, the base further includes a fixing hole. The positioning unit includes a second arcuate portion and a positioning member. The second arcuate portion has an arcuate slot. The positioning member extends through the arcuate slot and is engaged in the fixing hole of the base to prevent movement of the rotating unit and the positioning unit of the driving and positioning device.

In an example, each of the at least three action units further includes a body having an upper face with a recessed portion extending in a radial direction perpendicular to the central axis. Each sliding member is received in one of the recessed portions to provide a positioning effect for the sliding member.

In an example, the body of each of the at least three action units further includes a first groove defined in the upper face thereof, extending in a circumferential direction surrounding the central axis, and intercommunicating with the recessed portion. The rotating unit is received in the first grooves. An easy-to-assemble effect is, thus, provided.

In an example, the body of each of the at least three action units further includes a second groove defined in a lower face thereof and extending in a circumferential direction surrounding the central axis. Each second groove is coupled with the base. An easy-to-assemble effect is, thus, provided.

In an example, each of the at least three action units further includes two limiting blocks and a plurality of first fasteners. Each of the two limiting blocks includes a plurality of limiting holes. The body of each of the at least three action units further includes a plurality of assembling holes. Each of the plurality of first fasteners extends through one of the plurality of limiting holes and one of the plurality of assembling holes. Thus, each of the two limiting blocks can be fixed on a corresponding one of the bodies.

In an example, the body of each of the at least three action units further includes a plurality of first engaging holes and a plurality of second fasteners. Each of the plurality of second fasteners extends through one of the plurality of first engaging holes and tightly presses against the base. Thus, the body of each of the at least three action units can be fixed on the base.

In an example, each sliding member further includes an abutting portion on an end face of the sliding member facing the central axis. The abutting portion of each sliding member is substantially arcuate for intimate contact with the outer periphery of the reception end.

The present invention will become clearer in light of the following detailed description of illustrative embodiments of this invention described in connection with the drawings.

DETAILED DESCRIPTION

Figure 1:
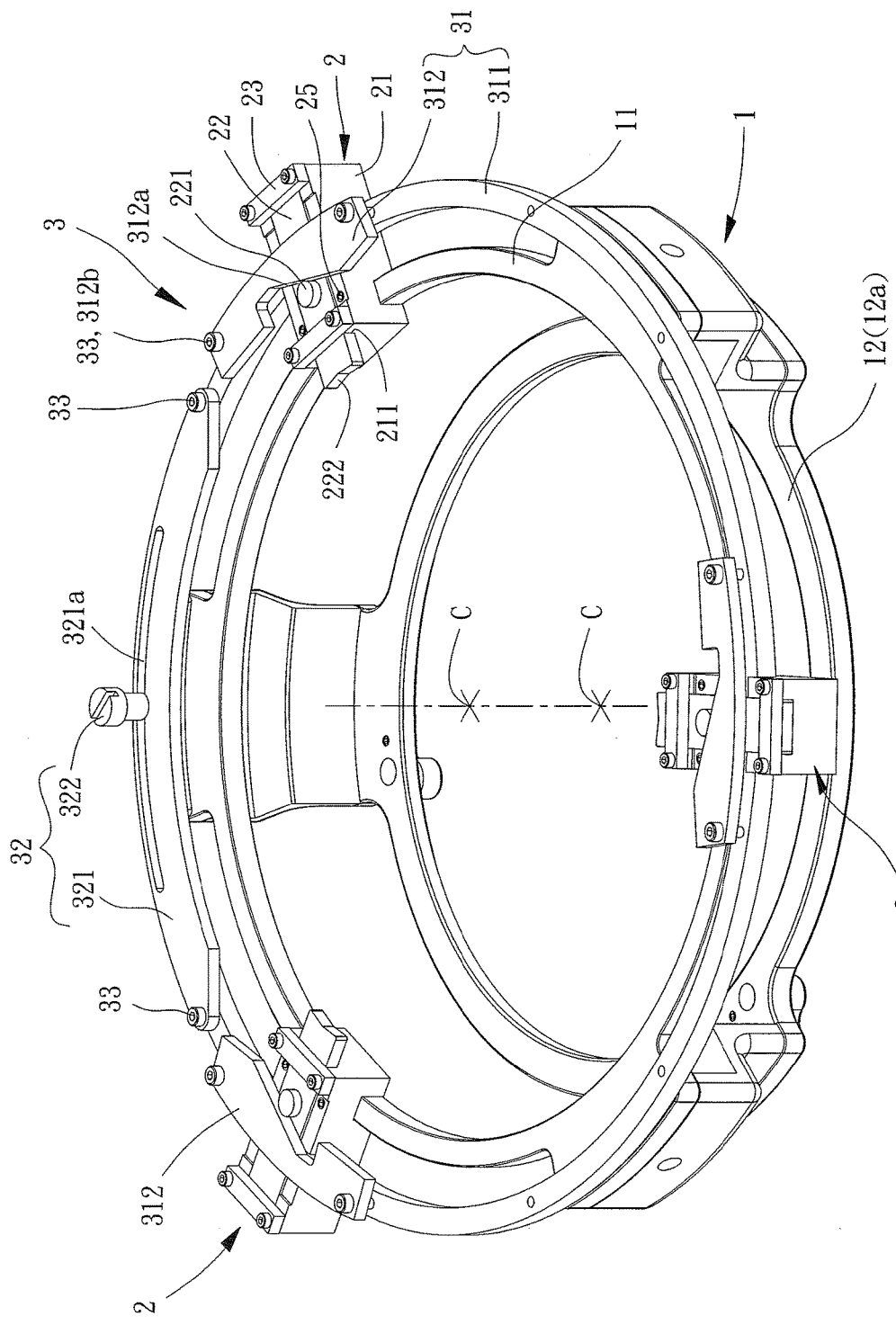
FIG. 1 is a perspective view of a universal C-arm calibration seat of an embodiment according to the present invention.
Figure 2:
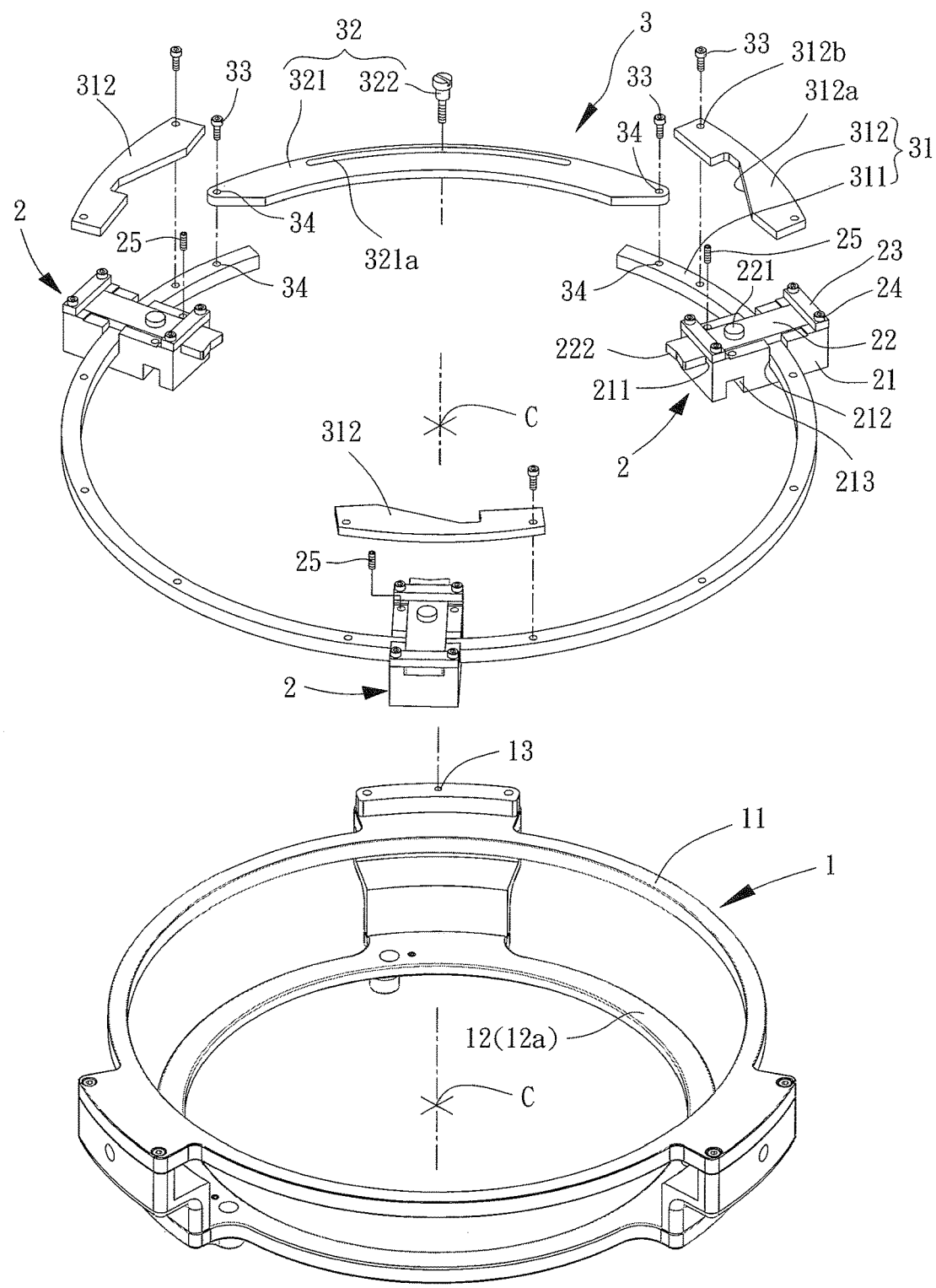
FIG. 2 is an exploded, perspective view of the universal C-arm calibration seat of FIG. 1.

With reference to FIGS. 1 and 2, a universal C-ARM calibration seat of an embodiment according to the present invention includes a base 1, at least three action units 2, and a driving and positioning device 3. The at least three action units 2 are mounted on the base 1. The driving and positioning device 3 is coupled with each of the at least three action units 2.

With reference to FIGS. 1 and 2, the base 1 includes a first annular member 11 and a second annular member 12 coaxial to the first annular member 11. Namely, the base 1 is annular and has a central axis C. The second annular member 12 provides a calibration plate mounting area 12a on which a calibration plate 4 (FIG. 7) can be disposed. The base 1 further includes a fixing hole 13 defined in an upper side of the first annular member 11.

Figure 3:
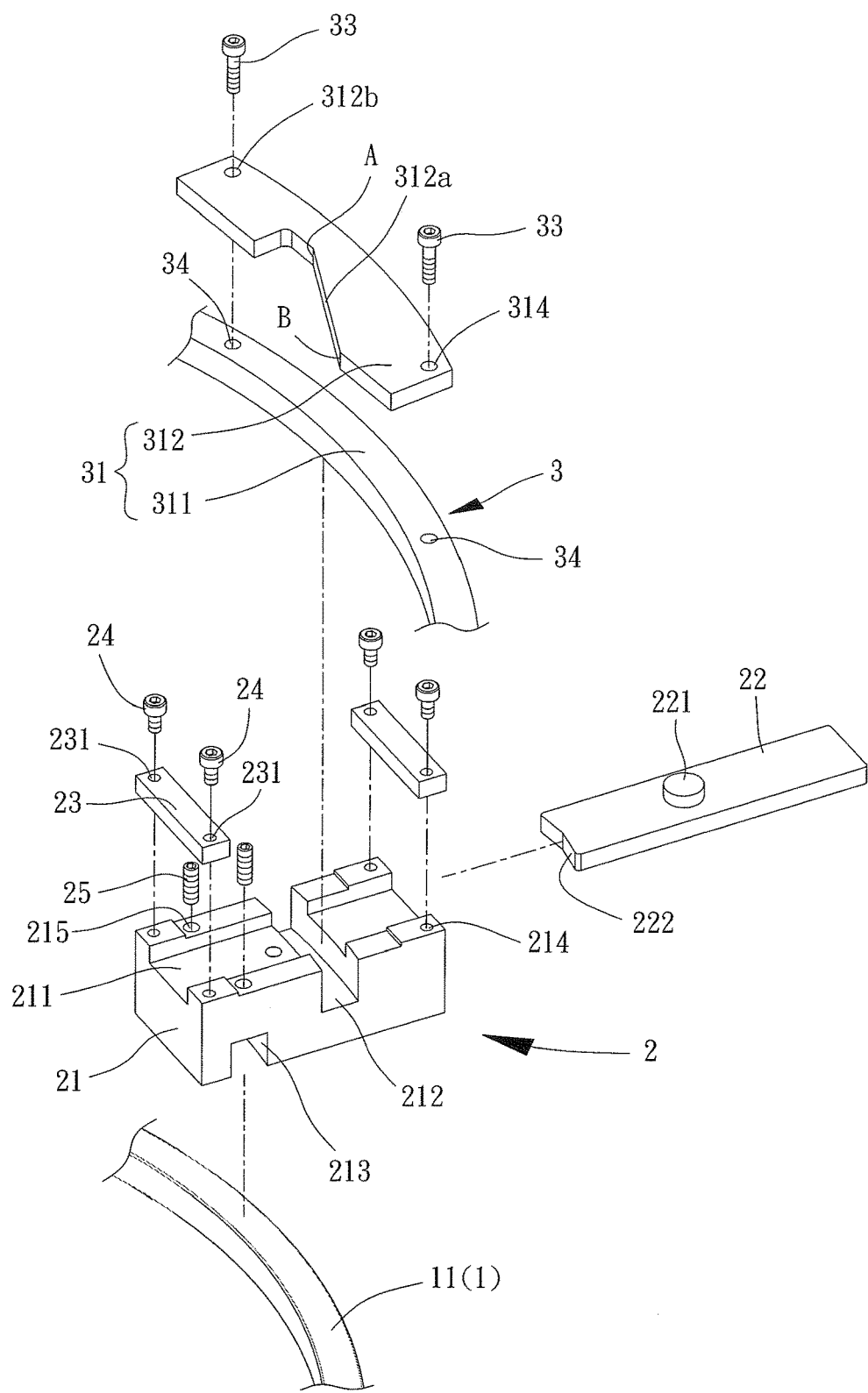
FIG. 3 is a partial, perspective view of the universal C-arm calibration seat of FIG. 1.

With reference to FIGS. 2 and 3, the at least three action units 2 are mounted on a side of the base 1 opposite to the calibration plate mounting area 12a. Each of the at least three action units 2 includes a body 21 and a sliding member 22 that can displace reciprocatingly. The body 21 of each of the at least three action units 2 includes an upper face having a recessed portion 211 extending in a radial direction perpendicular to the central axis C. The body 21 of each of the at least three action units 2 further includes a first groove 212 defined in the upper face thereof, extending in a circumferential direction surrounding the central axis C, and intercommunicating with the recessed portion 211. The body 21 of each of the at least three action units 2 further includes a second groove 213 defined in a lower face thereof and extending in a circumferential direction surrounding the central axis C. Each second groove 213 is coupled with the first annular member 11 of the base 1 to couple each of the at least three action units 2 to the first annular member 11 of the base 1. The upper face of the body 21 of each of the at least three action units 2 further includes a plurality of assembling holes 214 and a plurality of first engaging holes 215. Each sliding member 22 is received in one of the recessed portions 211 and includes an upper face having a protrusion 221. When the sliding members 22 are respectively received in the recessed portions 211, the protrusion 221 of each sliding member 22 protrudes beyond the upper face of the corresponding body 21. Each sliding member 22 further includes an abutting portion 222 on an end face of the sliding member 22 facing the central axis C. The abutting portion 222 of each sliding member 22 is substantially arcuate.

With reference to FIGS. 2 and 3, each of the at least three action units 2 further includes two limiting blocks 23 and a plurality of first fasteners 24. Each of the two limiting blocks 23 includes a plurality of limiting holes 231. Each of the plurality of first fasteners 24 extends through one of the plurality of limiting holes 231 and one of the plurality of assembling holes 214. Thus, the two limiting blocks 23 are fixed on the body 21 to prevent the sliding member 22 from disengaging from the recessed portion 211 of the body 21. Furthermore, each of the at least three action units 2 includes a plurality of second fasteners 25. Each of the plurality of second fasteners 25 extends through one of the plurality of first engaging holes 215 and tightly presses against the first annular member 11 of the base 1, thereby fixing the body 21 to the first annular member 11 of the base 1.

With reference to FIGS. 2 and 3, the driving and positioning device 3 is coaxially mounted to and rotatable relative to the base 1 about the central axis C. The driving and positioning device 3 includes a rotating unit 31 and a positioning unit 32. Each of the rotating unit 31 and the positioning unit 32 includes a plurality of second engaging holes 34. A plurality of fasteners 33 extends through the plurality of second engaging holes 34 of the rotating unit 31 and the positioning unit 32 to couple the rotating unit 31 and the positioning unit 32 together.

With reference to FIGS. 2 and 3, the rotating unit 31 includes a first arcuate plate 311 and at least three engaging plates 312. The first arcuate plate 311 is received in the first grooves 212 of the bodies 21 of the at least three action units 2 and is, thus, disposed between the body 21 and the sliding member 22 of each of the at least three action units 2. Furthermore, each of the at least three engaging plates 312 is disposed in association with one of the at least three action units 2 and is fixed to the first arcuate plate 311. Each of the at least three engaging plates 312 includes an inclined portion 312a for abutting the protrusion 221 of a corresponding one of the sliding members 22. Each of the at least three engaging plates 312 further includes a plurality of third engaging holes 312b. Each of the plurality of fasteners 33 extends through one of the plurality of third engaging holes 312b and one of the plurality of second engaging holes 34 to fix each of the at least three engaging plates 312 to the first arcuate plate 311. Furthermore, the positioning unit 32 includes a second arcuate portion 321 and a positioning member 322. The second arcuate portion 321 has an arcuate slot 321a extending from an upper face through a lower face of the second arcuate portion 321. The positioning member 322 of the positioning unit 32 extends through the arcuate slot 321a and is engaged in the fixing hole 13 of the base 1.

Figure 4:
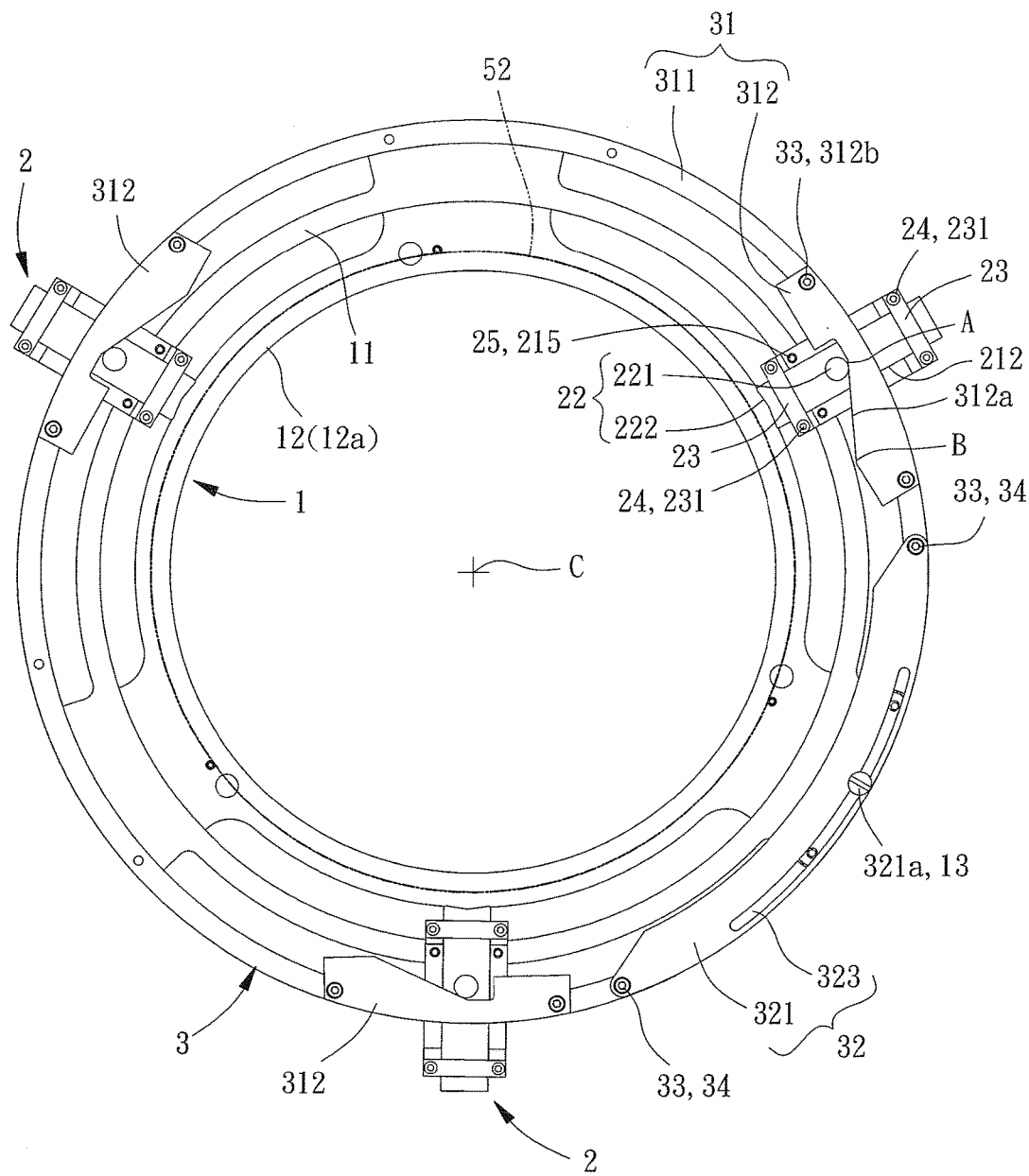
FIG. 4 is a top view of the universal C-arm calibration seat of FIG. 1.
Figure 5:
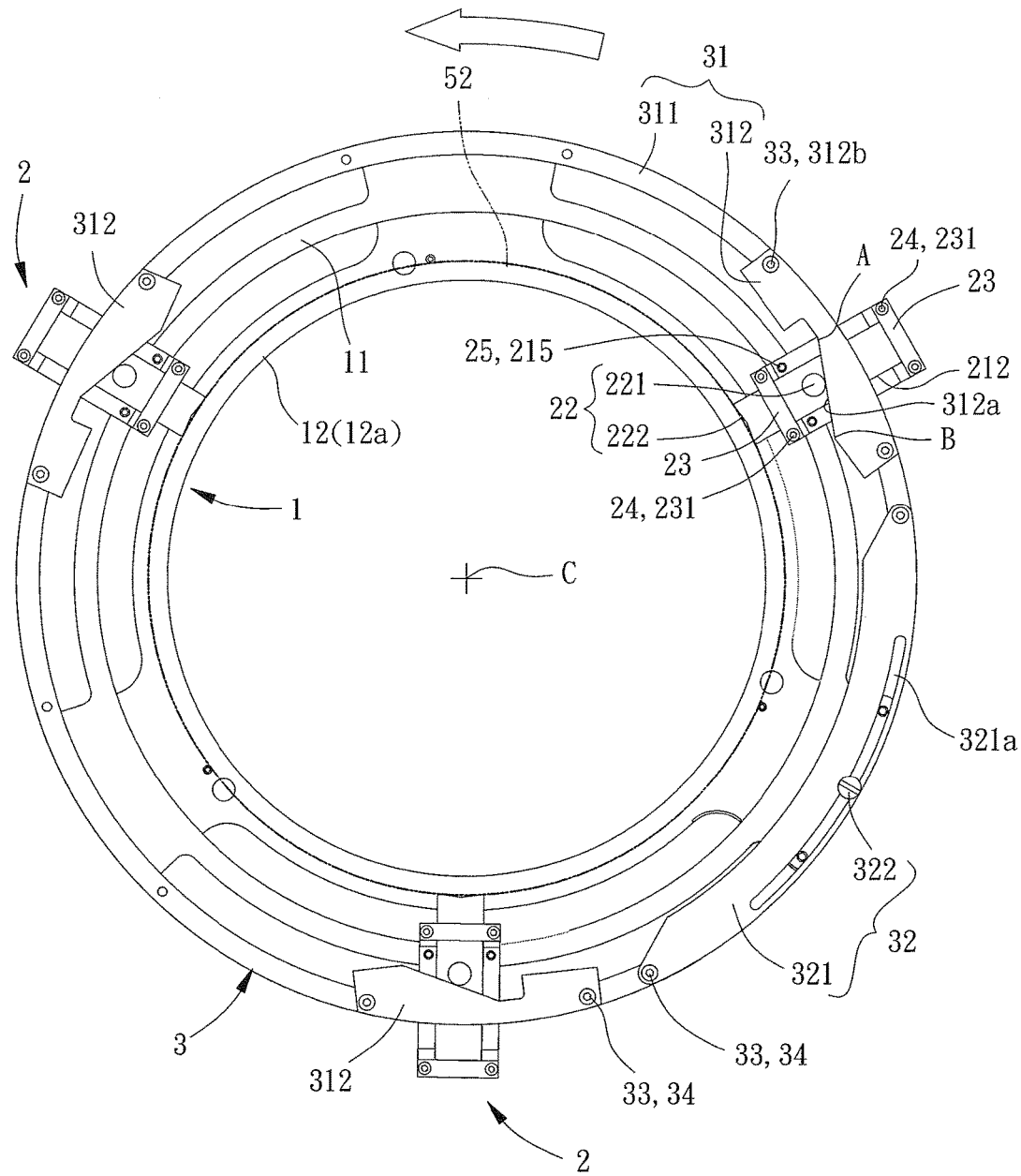
FIG. 5 is a top view illustrating operation of the universal C-arm calibration seat of FIG. 4.

With reference to FIGS. 3-5, specifically, the inclined portion 312a of each of the at least three engaging plates 312 includes a start point A and an end point B. When the at least three engaging plates 312 are driven by the first arcuate plate 311 to rotate in the counterclockwise direction, the inclined portion 312a of each of the at least three engaging plates 312 presses against a corresponding one of the protrusions 221, such that the protrusion 221 of each sliding member 22 moves from the start point A toward the end point B of a corresponding one of the inclined portions 312a. As a result, each sliding member 22 moves toward the central axis C.

Figure 6:
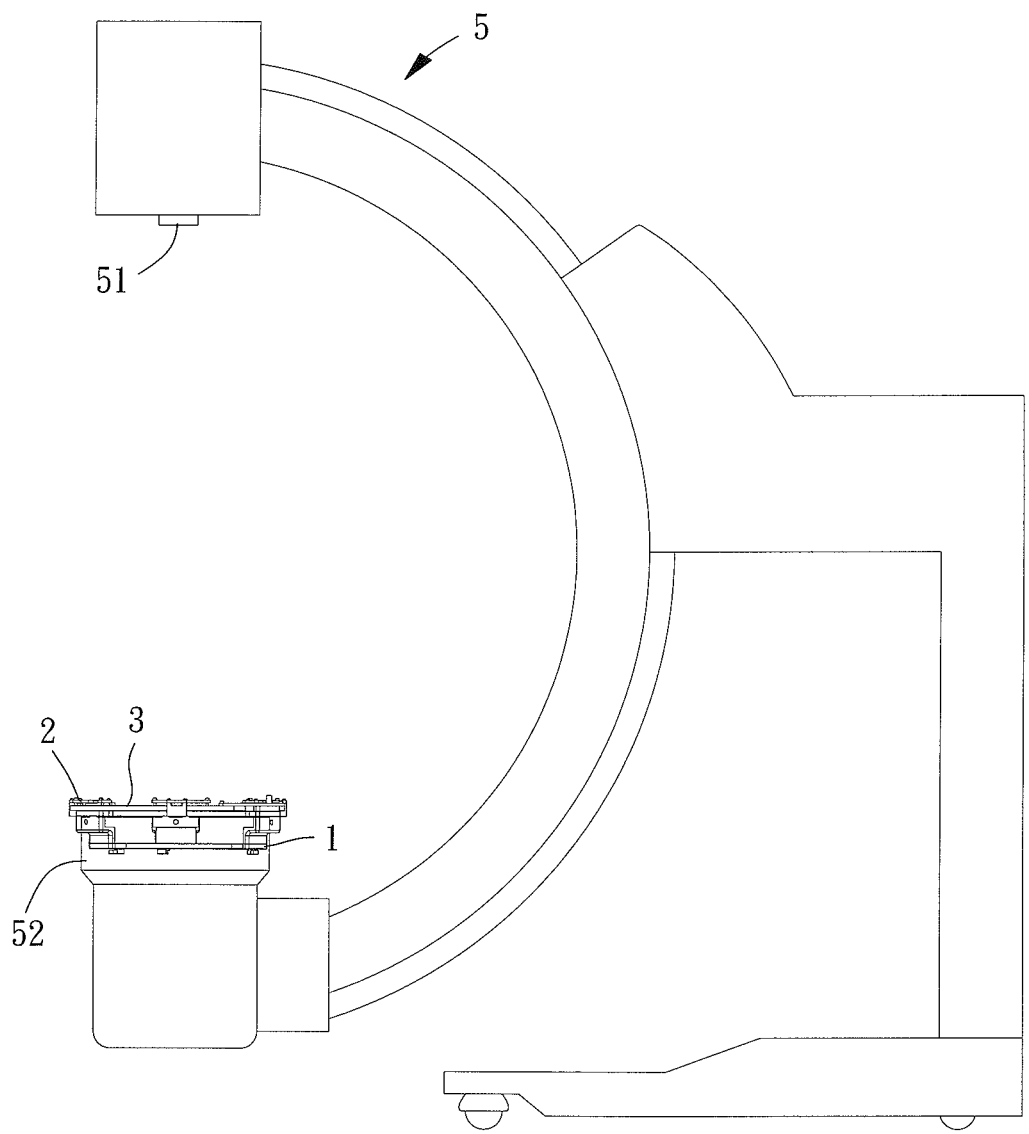
FIG. 6 is a diagrammatic view illustrating use of the universal C-arm calibration seat of an embodiment according to the present invention on C-arm equipment.

With reference to FIGS. 4-6, according to the above structure, the universal C-arm calibration seat in use is coupled to 2D C-arm equipment 5 including a transmitting end 51 and a reception end 52. The reception end 52 is cylindrical. The universal C-arm calibration seat is coupled to the reception end 52. Specifically, the second annular member 12 of the base 1 is disposed on an upper edge of the reception end 52 of the 2D C-arm equipment 5 to avoid the whole universal C-arm calibration seat from falling from the reception end 52. Furthermore, a calibration plate 4 (FIG. 7) is disposed on the calibration plate mounting area 12a provided by the second annular member 12.

Figure 7:
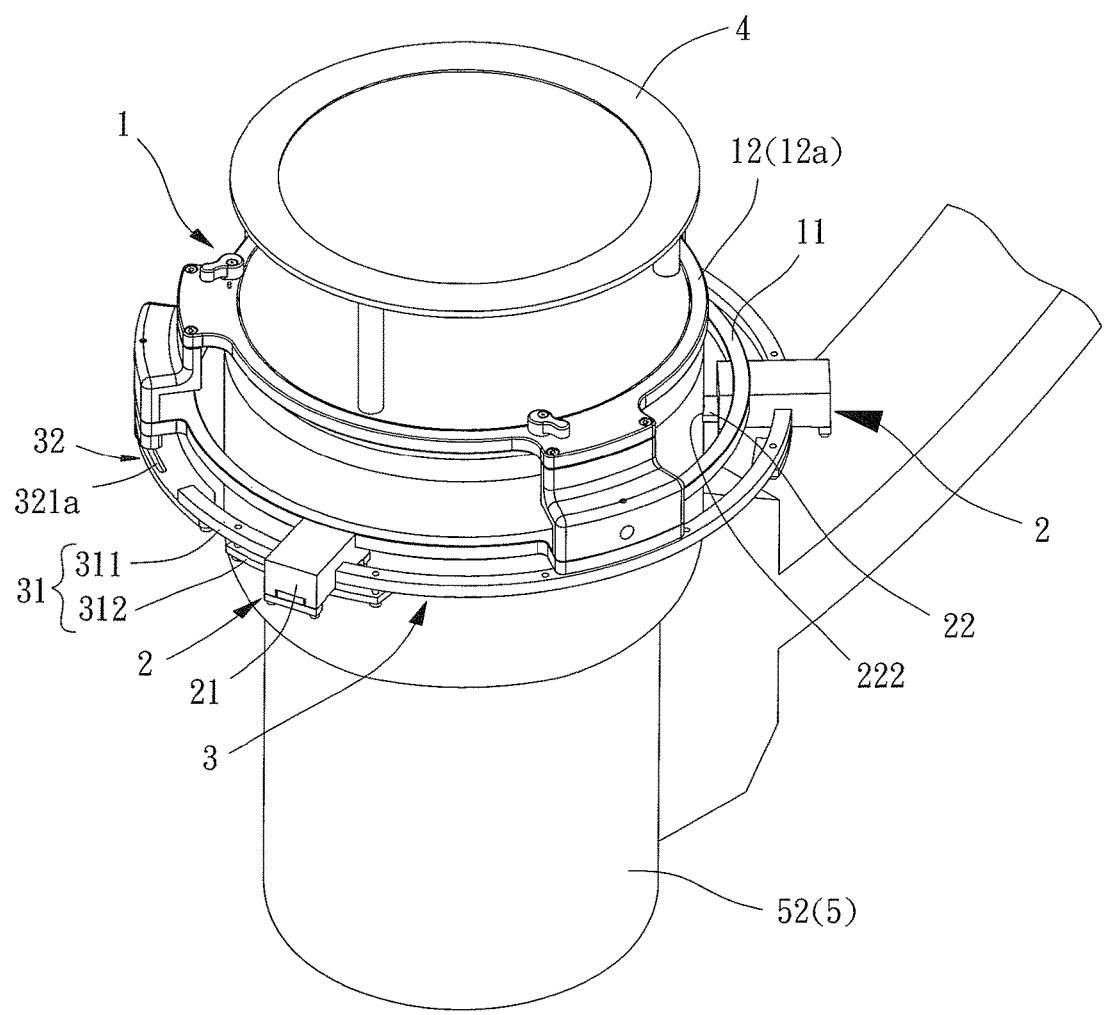
FIG. 7 is an enlarged, perspective view of a portion of FIG. 6.

With reference to FIGS. 5-7, when the rotating unit 31 of the driving and positioning device 3 is rotated counterclockwise, the positioning unit 32 is driven to move in the counterclockwise direction. Since the inclined portion 312a of each of the at least three engaging plates 312 presses against a corresponding one of the protrusions 221, the protrusion 221 of each sliding member 22 moves from the start point A toward the end point B of the inclined portion 312a of a corresponding one of the at least three engaging plates 312. Thus, all sliding members 22 simultaneously move toward the central axis C until the abutting portion 222 of each sliding member 22 abuts an outer periphery of the reception end 52 of the 2D C-arm equipment 5. The abutting portion 222 of each sliding member 22 is substantially arcuate to be in intimate contact with the outer periphery of the reception end 52 of the 2D C-arm equipment 5. Then, the positioning member 322 of the driving and positioning device 3 can be rotated to a tightened state to avoid displacement of the rotating unit 31 of the driving and positioning device 3. As a result, the abutting portion 222 of each sliding member 22 will not displace and, thus, will not disengage from the outer periphery of the reception end 52.

In view of the foregoing, the universal C-arm calibration seat according to the present invention uses the interrelationship between the driving and positioning device 3 and the at least three action units 2, such that when the rotating unit 31 of the driving and positioning device 3 rotates in the counterclockwise direction, the inclined portion 312a of each of the at least three engaging plates 312 presses against a corresponding one of the protrusions 221. Thus, all sliding members 22 simultaneously move toward the central axis C until the abutting portion 222 of each sliding member 22 abuts the outer periphery of the reception end 52 of the 2D C-arm equipment 5. Then, the positioning member 322 of the driving and positioning device 3 is rotated to a tightened state to achieve a coaxial positioning effect. In addition to easy installation, the universal C-arm calibration seat according to the present invention is suitable for use with all conventional X-ray machines with a 2D C-arm.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:
1. A universal C-ARM calibration seat comprising:
a base, wherein the base is annular and has a central axis, and wherein the base includes a correction plate mounting area;
at least three action units mounted on a side of the base opposite to the correction plate mounting area, wherein each of the at least three action units includes a sliding member; and
a driving and positioning device coaxially mounted to and rotatable relative to the base about the central axis, wherein the driving and positioning device includes a rotating unit configured to actuate each sliding member, wherein when the driving and positioning device rotates relative to the base, the rotating unit actuates each sliding member to simultaneously move toward the central axis.

2. The universal C-ARM calibration seat as claimed in claim 1, wherein the driving and positioning device includes a positioning unit, wherein when each sliding member is displaced to a predetermined position, the positioning unit restrains rotation of the rotating unit relative to the base.

3. The universal C-ARM calibration seat as claimed in claim 1, wherein the rotating unit includes a first arcuate plate and at least three engaging plates, wherein the first arcuate plate extends through each of the at least three action units, wherein each of the at least three engaging plates is disposed in association with one of the at least three action units and is fixed to the first arcuate plate, wherein each of the at least three engaging plates includes an inclined portion, wherein each sliding member includes an upper face having a protrusion, and wherein the inclined portion of each of the at least three engaging plates abuts the protrusion of one of the sliding members.

4. The universal C-ARM calibration seat as claimed in claim 2, wherein the base further includes a fixing hole, wherein the positioning unit includes a second arcuate portion and a positioning member, wherein the second arcuate portion has an arcuate slot, wherein the positioning member extends through the arcuate slot and is engaged in the fixing hole of the base.

5. The universal C-ARM calibration seat as claimed in claim 1, wherein each of the at least three action units further includes a body having an upper face with a recessed portion extending in a radial direction perpendicular to the central axis, and wherein each sliding member is received in one of the recessed portions.

6. The universal C-ARM calibration seat as claimed in claim 5, wherein the body of each of the at least three action units further includes a first groove defined in the upper face thereof, extending in a circumferential direction surrounding the central axis, and intercommunicating with the recessed portion, and wherein the rotating unit is received in the first grooves.

7. The universal C-ARM calibration seat as claimed in claim 5, wherein the body of each of the at least three action units further includes a second groove defined in a lower face thereof and extending in a circumferential direction surrounding the central axis, and wherein each second groove is coupled with the base.

8. The universal C-ARM calibration seat as claimed in claim 5, wherein each of the at least three action units further includes two limiting blocks and a plurality of first fasteners, wherein each of the two limiting blocks includes a plurality of limiting holes, wherein the body of each of the at least three action units further includes a plurality of assembling holes, wherein each of the plurality of first fasteners extends through one of the plurality of limiting holes and one of the plurality of assembling holes.

9. The universal C-ARM calibration seat as claimed in claim 8, wherein the body of each of the at least three action units further includes a plurality of first engaging holes and a plurality of second fasteners, wherein each of the plurality of second fasteners extends through one of the plurality of first engaging holes and tightly presses against the base.

10. The universal C-ARM calibration seat as claimed in claim 1, wherein each sliding member further includes an abutting portion on an end face of the sliding member facing the central axis, and wherein the abutting portion of each sliding member is substantially arcuate.

\* \* \* \* \*